(12) United States Patent
Llinas et al.

(10) Patent No.: US 10,080,555 B2
(45) Date of Patent: Sep. 25, 2018

(54) METHODS AND PRODUCTS FOR REDUCING TISSUE TRAUMA USING WATER-ABSORBING STRESS-DISTRIBUTING MATERIALS

(75) Inventors: Adolfo M. Llinas, Bogata (CO); Stephen E. Krampe, Maplewood, MN (US); Matthew T. Scholz, Woodbury, MN (US); Patrick J. Parks, Mendota Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 590 days.

(21) Appl. No.: 13/391,225

(22) PCT Filed: Aug. 21, 2009

(86) PCT No.: PCT/US2009/054662
§ 371 (c)(1),
(2), (4) Date: Jun. 6, 2012

(87) PCT Pub. No.: WO2011/022023
PCT Pub. Date: Feb. 24, 2011

(65) Prior Publication Data
US 2012/0247487 A1   Oct. 4, 2012

(51) Int. Cl.
*A61B 17/02*        (2006.01)
*A61F 13/00*        (2006.01)
(Continued)

(52) U.S. Cl.
CPC ............ *A61B 17/02* (2013.01); *A61B 46/00* (2016.02); *A61B 90/04* (2016.02);
(Continued)

(58) Field of Classification Search
CPC ... A61B 19/08; A61B 2046/205; A61B 46/20; A61B 46/10; A61B 46/13; A61B 46/17; A61B 2046/201; A61B 46/30; A61B 90/40; A61B 2017/00942; A61F 13/00038; A61F 13/00029; A61F 13/00025; A61F 13/0213;
(Continued)

(56) References Cited

U.S. PATENT DOCUMENTS

| 477,943 A | 6/1892 | Kimble |
| 2,736,721 A | 2/1956 | Dexter |

(Continued)

FOREIGN PATENT DOCUMENTS

| EP | 0 264 299 | 4/1988 |
| EP | 0 621 042 | 10/1994 |

(Continued)

OTHER PUBLICATIONS

ASTM D412—06a, Standard Test methods for Vulcanized Rubber Thermoplastic Elastomers-Tension, 2006, 14 pages.
(Continued)

*Primary Examiner* — Kari Rodriquez
*Assistant Examiner* — Camtu Nguyen

(57) ABSTRACT

Methods and products for protecting tissue of a patient during a surgical procedure that involve making an incision in the tissue and retracting the tissue to make a larger opening, wherein the methods and products use a water-absorbing stress-distributing layer.

12 Claims, 3 Drawing Sheets

(51) Int. Cl.
*A61F 13/02* (2006.01)
*A61B 90/00* (2016.01)
*A61B 46/00* (2016.01)
A61B 17/00 (2006.01)
A61F 13/15 (2006.01)
A61F 13/45 (2006.01)
A61B 46/20 (2016.01)
A61B 90/40 (2016.01)

(52) U.S. Cl.
CPC .. *A61F 13/00025* (2013.01); *A61F 13/00029* (2013.01); *A61F 13/00038* (2013.01); *A61F 13/0213* (2013.01); A61B 90/40 (2016.02); A61B 2017/00942 (2013.01); A61B 2046/205 (2016.02); A61F 2013/00182 (2013.01); A61F 2013/00272 (2013.01); A61F 2013/00306 (2013.01); A61F 2013/00387 (2013.01); A61F 2013/00676 (2013.01); A61F 2013/00846 (2013.01); A61F 2013/15073 (2013.01); A61F 2013/4593 (2013.01)

(58) Field of Classification Search
CPC .... A61F 2013/4593; A61F 2013/15073; A61F 2013/00182; A61F 2013/00272; A61F 2013/00306; A61F 2013/00387; A61F 2013/00676
USPC .......................................... 128/849–850, 855
See application file for complete search history.

(56) References Cited

U.S. PATENT DOCUMENTS

| | | | |
|---|---|---|---|
| 3,146,884 A | 9/1964 | Pereny et al. | |
| 3,260,260 A | 7/1966 | Questel | |
| 3,347,226 A | 10/1967 | Harrower | |
| 3,669,106 A | 6/1972 | Schrading et al. | |
| 3,822,238 A | 7/1974 | Blair | |
| 3,856,006 A | 12/1974 | Krzewinski | |
| 3,916,887 A | 11/1975 | Kelly | |
| 3,916,910 A | 11/1975 | Seeling et al. | |
| 3,975,350 A | 8/1976 | Hudgin | |
| 4,027,665 A * | 6/1977 | Scrivens | A61B 46/00 128/854 |
| 4,169,472 A | 10/1979 | Morris | |
| 4,231,369 A | 11/1980 | Sorensen | |
| 4,310,509 A | 1/1982 | Berglund | |
| 4,323,557 A | 4/1982 | Rosso | |
| 4,369,294 A | 1/1983 | Stoy | |
| 4,374,520 A | 2/1983 | Grossmann et al. | |
| 4,379,874 A | 4/1983 | Stoy | |
| 4,420,589 A | 12/1983 | Stoy | |
| 4,427,737 A * | 1/1984 | Cilento et al. | 428/315.7 |
| 4,452,845 A | 6/1984 | Lloyd | |
| 4,454,309 A | 6/1984 | Gould | |
| 4,477,325 A | 10/1984 | Osburn | |
| 4,499,896 A | 2/1985 | Heinecke | |
| RE31,886 E | 5/1985 | Hodgson | |
| RE31,887 E | 5/1985 | Hodgson | |
| 4,542,012 A | 9/1985 | Dell | |
| 4,551,490 A | 11/1985 | Doyle | |
| 4,554,324 A | 11/1985 | Husman | |
| 4,584,192 A | 4/1986 | Dell | |
| 4,621,619 A * | 11/1986 | Sharpe | A61B 17/02 128/DIG. 15 |
| 4,737,559 A | 4/1988 | Kellen | |
| 4,738,257 A | 4/1988 | Meyer | |
| 4,777,943 A | 10/1988 | Chvapil | |
| 4,820,279 A | 4/1989 | Dedo | |
| 4,899,762 A * | 2/1990 | Muller | A61B 17/085 128/850 |
| 5,087,499 A | 2/1992 | Sullivan | |
| 5,197,493 A | 3/1993 | Grier-Idris | |
| 5,214,119 A | 5/1993 | Leir | |
| 5,270,358 A * | 12/1993 | Asmus | A61L 24/043 424/448 |
| 5,369,155 A | 11/1994 | Asmus | |
| 5,506,279 A | 4/1996 | Babu | |
| 5,507,765 A | 4/1996 | Mott | |
| 5,524,644 A | 6/1996 | Crook | |
| 5,593,395 A | 1/1997 | Martz | |
| 5,633,010 A | 5/1997 | Chen | |
| 5,709,646 A | 1/1998 | Lange | |
| 5,730,994 A * | 3/1998 | Askill | A61L 15/24 424/402 |
| 5,750,134 A | 5/1998 | Scholz | |
| 5,783,504 A | 7/1998 | Ehret et al. | |
| 5,803,086 A | 9/1998 | Scholz | |
| 5,825,543 A | 10/1998 | Ouderkirk | |
| 5,828,488 A | 10/1998 | Ouderkirk | |
| 5,829,422 A | 11/1998 | Deeds | |
| 5,867,316 A | 2/1999 | Carlson | |
| 5,882,774 A | 3/1999 | Jonza | |
| 5,979,450 A | 11/1999 | Baker | |
| 5,979,452 A | 11/1999 | Fogarty et al. | |
| 5,985,395 A | 11/1999 | Comstock | |
| 6,033,604 A | 3/2000 | Lundin | |
| 6,083,856 A | 7/2000 | Joseph | |
| 6,179,948 B1 | 1/2001 | Merrill | |
| 6,216,699 B1 | 4/2001 | Cox | |
| 6,245,959 B1 | 6/2001 | Ohira et al. | |
| 6,264,976 B1 | 7/2001 | Heinecke | |
| 6,288,172 B1 | 9/2001 | Goetz | |
| 6,352,761 B1 | 3/2002 | Hebrink | |
| 6,367,941 B2 | 4/2002 | Lea | |
| 6,368,699 B1 | 4/2002 | Gilbert | |
| 6,436,432 B2 | 8/2002 | Heinecke | |
| 6,566,575 B1 | 5/2003 | Stickels | |
| 6,663,978 B1 | 12/2003 | Olson | |
| 6,827,886 B2 | 12/2004 | Neavin | |
| 6,845,212 B2 | 1/2005 | Gardiner | |
| 6,855,386 B1 | 2/2005 | Daniels | |
| 6,927,900 B2 | 8/2005 | Liu | |
| 6,939,296 B2 | 9/2005 | Ewers | |
| 6,939,936 B2 | 9/2005 | Wang | |
| 6,972,813 B1 | 12/2005 | Toyooka | |
| 6,991,695 B2 | 1/2006 | Tait | |
| 7,030,203 B2 | 4/2006 | Mosbey | |
| 7,046,905 B1 | 5/2006 | Gardiner | |
| 7,090,922 B2 | 8/2006 | Zhou | |
| 7,255,920 B2 | 8/2007 | Everaerts | |
| 7,315,418 B2 | 1/2008 | DiZio | |
| 7,361,474 B2 | 4/2008 | Siegler | |
| 7,459,167 B1 | 12/2008 | Sengupta | |
| 7,481,563 B2 | 1/2009 | David | |
| 7,879,078 B2 | 2/2011 | Vardanega | |
| 2003/0034445 A1 | 2/2003 | Boyd | |
| 2003/0121522 A1 | 7/2003 | Gingles et al. | |
| 2004/0126413 A1 | 7/2004 | Sigurjonsson et al. | |
| 2004/0133143 A1 | 7/2004 | Burton et al. | |
| 2004/0254512 A1 | 12/2004 | Paturu | |
| 2005/0284487 A1 | 12/2005 | Gellerstedt et al. | |
| 2006/0084780 A1 | 4/2006 | Hebrink | |
| 2006/0216524 A1 | 9/2006 | Klun | |
| 2006/0226561 A1 | 10/2006 | Merrill | |
| 2007/0047080 A1 | 3/2007 | Stover | |
| 2007/0147947 A1 | 6/2007 | Stenton | |
| 2007/0223252 A1 | 9/2007 | Lee | |
| 2008/0046004 A1 | 2/2008 | Stenton | |
| 2008/0232135 A1 | 9/2008 | Kinder | |
| 2009/0067151 A1 | 3/2009 | Sahlin | |
| 2009/0105437 A1 | 4/2009 | Determan | |
| 2009/0116801 A1 | 5/2009 | Fine | |
| 2009/0187130 A1 | 7/2009 | Asmus | |
| 2009/0216170 A1* | 8/2009 | Robinson et al. | 602/60 |
| 2010/0222496 A1 | 9/2010 | Determan | |
| 2011/0134623 A1 | 6/2011 | Sherman | |
| 2011/0166492 A1 | 7/2011 | Asmus | |
| 2011/0176325 A1 | 7/2011 | Sherman | |
| 2011/0182076 A1 | 7/2011 | Sherman | |
| 2011/0313048 A1 | 12/2011 | Yang et al. | |

(56) References Cited

U.S. PATENT DOCUMENTS

| | | |
|---|---|---|
| 2012/0100039 A1 | 4/2012 | Appeaning |
| 2012/0215073 A1 | 8/2012 | Sherman |
| 2012/0240942 A1 | 9/2012 | Llinas |

FOREIGN PATENT DOCUMENTS

| | | |
|---|---|---|
| EP | 1 020 198 | 7/2000 |
| GB | 692578 | 6/1953 |
| GB | 2 089 351 | 6/1982 |
| JP | 2007-229520 | 9/2007 |
| WO | WO 1981/02100 | 8/1981 |
| WO | WO 84/01285 | 4/1984 |
| WO | WO 95/17303 | 6/1995 |
| WO | WO 95/17691 | 6/1995 |
| WO | WO 95/17692 | 6/1995 |
| WO | WO 95/17699 | 6/1995 |
| WO | WO 96/19347 | 6/1996 |
| WO | WO 97/01440 | 1/1997 |
| WO | WO 97/42902 A1 | 11/1997 |
| WO | WO 98/51352 | 11/1998 |
| WO | WO 99/36248 | 7/1999 |
| WO | WO 99/36262 | 7/1999 |
| WO | WO 99/42536 | 8/1999 |
| WO | WO 00/56828 | 9/2000 |
| WO | WO 00/78885 | 12/2000 |
| WO | WO 02/070237 | 9/2002 |
| WO | WO 2008/022007 | 2/2008 |
| WO | WO 2008/047059 | 4/2008 |
| WO | WO 2009/088757 | 7/2009 |
| WO | WO 2009/091682 | 7/2009 |
| WO | WO 2011/022023 | 2/2011 |
| WO | WO 2011/022525 | 2/2011 |
| WO | WO 2011/022527 | 2/2011 |

OTHER PUBLICATIONS

ASTM D5279—08, Standard Test Method for Plastics: Dynamic Mechanical Properties: In Torsion, 2008, 4 pages.

Corr, "Biomechanical behavior of scar tissue and uninjured skin in a porcine model", Wound Repair and Regeneration, Mar./Apr. 2009, vol. 17, No. 2, pp. 250-259.

Falk, "Seeing the Light", "Optics in Nature, Photography, Color, Vision, and Holography" 53-56 (1986).

Manschot,"The Measurement and Modelling of the Meachanical Properties of Human Skin In Vivo—I. The Measurement", Journal of Biomechanics, 1986, vol. 19. No. 7, pp. 511-515.

Satas, Handbook of Pressure Sensitive Adhesive Technology, Second Edition, (1989).

Stark, "Directional Variations in the Extensibility of Human Skin", British Journal of Plastic Surgery, Apr. 1977, vol. 30, No. 2, pp. 105-114.

Tegaderm CHG, Innovative Transparent Gel Pad, 2012, 1 page.

The Cutting Edge of Innovation, The story behind the development of 3M™ Ioban™ Antimicrobial Incise Drapes, 2012, 2 pages.

3M™ Tegaderm Tm Transparent Film Dressing Frame Style 1624W, 2012, 2 pages.

3M™ Tegasorb™ Hydrolloid Dressing, 90001, 2006, 1 page.

3M™ Tegaderm™ Hydrocolloid Dressing, 90002, 2012, 2 pages.

3M™ Tegaderm™ Hydrocolloid Dressing 90003, 2012, 2 pages.

International Search Report for PCT/US2009/054662, dated Oct. 6, 2009, 3 pages.

International Search Report for PCT/US2010/045956, dated Oct. 20, 2010, 3 pages.

International Search Report for PCT/US2010/045958, dated Jan. 19, 2011, 6 pages.

Written Opinion for PCT/US2009/054662, dated Oct. 6, 2009, 10 pages.

Written Opinion for PCT/US2010,045956, dated Oct. 20, 2010, 7 pages.

Written Opinion for PCT/US2010,045958, dated Jan. 19, 2011, 10 pages.

Declaration of Adolfo Llinas; 2 pgs. Signed Feb. 10, 2011.

Declaration of Patrick Parks; 3 pgs. Signed Jan. 25, 2011.

* cited by examiner

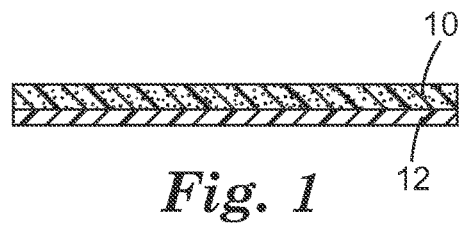
*Fig. 1*
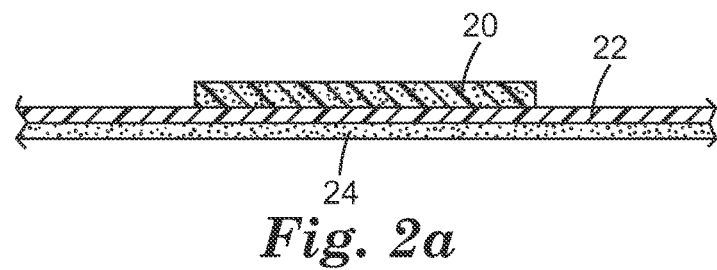
*Fig. 2a*
*Fig. 2b*
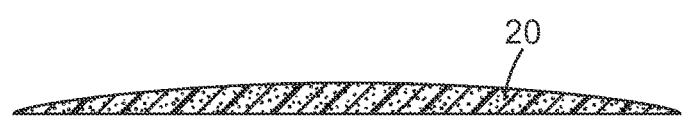
*Fig. 3a*
*Fig. 3b*
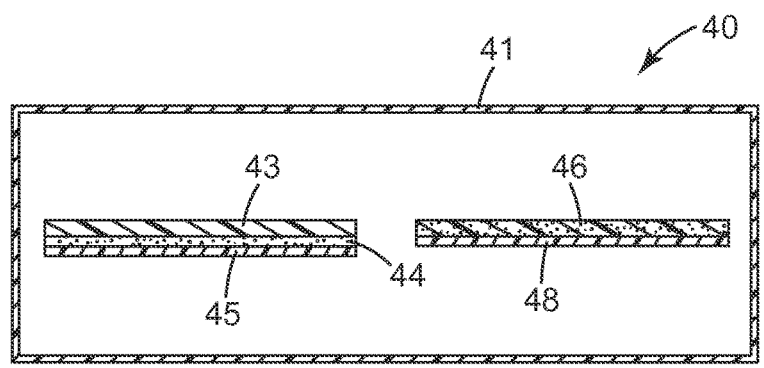
*Fig. 4*

METHODS AND PRODUCTS FOR REDUCING TISSUE TRAUMA USING WATER-ABSORBING STRESS-DISTRIBUTING MATERIALS

CROSS REFERENCE TO RELATED APPLICATIONS

This application is a national stage filing under 35 U.S.C. 371 of PCT/US2009/054662, filed Aug. 21, 2009, the disclosure of which is incorporated by reference in its entirety herein.

BACKGROUND

There is a move towards minimally invasive therapy in all areas of surgery in an effort to accelerate patient recovery, improve outcomes, and reduce costs. Current efforts in minimally invasive surgery in orthopedics includes, for example, a single incision hip replacement process where the incision is approximately 10 centimeters (cm) in length as opposed to the approximately 30 cm length used historically. Current literature refers to the shorter incision as a "reduced incision" process, with outcomes similar using either length incision; however, tissue trauma is generally greater with the shorter incision. Tissue trauma, especially at and near the incisional (i.e., wound) edge, can be a significant issue in open procedures as well. This tissue trauma can lead to more prominent scarring.

Surgical incise drapes are adhesive-coated organic polymeric drapes that are applied to the patient's skin typically after applying a presurgical preparation. The practitioner makes the incision right through the drape. In this manner, on the skin surface around the incisional site, the drape physically restricts the migration of bacteria remaining after the surgical prep procedure. Surgical incise drapes used during such surgeries have been designed to be very conformable and to have high adherence to the skin so as to allow surgical skin retraction without the drape lifting along the incisional edges. However, the materials used for the film and adhesive have not been designed to protect the skin from the trauma due to high compressive and/or stretching forces during tissue retraction which occurs in nearly all procedures to some degree. These forces, particularly after prolonged retraction through the surgical procedure, cause capillary blood flow disruption which can lead to tissue necrosis, significant bruising, and/or nerve damage with the potential of long term postoperative pain. Furthermore, prolonged retraction under significant force also may stretch the skin along the wound edge making reapposition post surgery difficult. There is a need to reduce such incisional stress and tissue trauma, thereby providing better patient outcomes by potentially faster healing and better cosmesis, a potential reduction in site infections, and possibly reduced post surgery pain.

SUMMARY

The present invention is directed to methods and products to protect tissue during a surgical procedure through the use of a stress-distributing layer. The use of such a material can assist in reducing incisional stress and tissue trauma by distributing the forces caused by refraction over a broad area, thereby providing the potential for one or more of the following: faster healing; better cosmesis; reduction in site infections; and reduced post surgery pain.

In one embodiment, the present invention provides a method of protecting tissue of a patient during a surgical procedure, wherein the method includes: providing a water-absorbing stress-distributing layer comprising a hydrogel, a hydrocolloid, or a combination thereof; wherein the stress-distributing layer has opposite first and second major surfaces and at least a portion of the stress-distributing layer is greater than 2 mm thick between the first and second major surfaces; adhering the stress-distributing layer to the patient such that it conforms to the shape of the tissue of the patient (wherein the tissue, e.g., skin, has typically been treated with a presurgical skin preparation); making an incision through the stress-distributing layer into the tissue; and refracting the tissue along the incision using a retractor; wherein the stress-distributing layer undergoes stretching and/or compression during retraction.

For all methods herein, preferably, the stress-distributing layer does not tear during retraction, and more preferably, it adheres sufficiently to the patient such that the refraction does not displace the stress-distributing layer from the patient along the incision while the stress-distributing layer undergoes stretching and/or compression.

In another embodiment, the present invention provides a method of protecting tissue of a patient during a surgical procedure, wherein the method includes: providing a flexible polymeric film having opposite first and second major surfaces; providing a water-absorbing stress-distributing layer comprising a hydrogel, a hydrocolloid, or a combination thereof; wherein the stress-distributing layer has opposite first and second major surfaces and at least a portion of the stress-distributing layer is at least 1 mm thick between the first and second major surfaces; placing the flexible polymeric film and the stress-distributing layer in contact with one another so that the flexible polymeric film and the stress-distributing layer are attached together to form a stress-distributing composite, and the stress-distributing composite is adhered to the patient such that the stress-distributing composite conforms to the shape of the tissue of the patient; making an incision through the stress-distributing composite into the tissue; and retracting the tissue along the incision using a refractor; wherein the stress-distributing composite undergoes stretching and/or compression during retraction.

In yet another embodiment, the present invention provides a method of protecting tissue of a patient during a surgical procedure, wherein the method includes: providing a surgical incise drape comprising a flexible polymeric film having opposite first and second major surfaces and a pressure sensitive adhesive on at least a portion of at least one major surface thereof; providing a free-standing water-absorbing stress-distributing layer comprising a hydrogel, a hydrocolloid, or a combination thereof; wherein the stress-distributing layer has opposite first and second major surfaces; adhering the surgical incise drape to the patient (wherein the tissue of the patient, e.g., skin, has typically been treated with a presurgical skin preparation); adhering the free-standing stress-distributing layer to the surgical incise drape; making an incision through the incise drape and the stress-distributing layer into the tissue; and retracting the tissue along the incision using a retractor; wherein the surgical incise drape and stress-distributing layer undergo stretching and/or compression during retraction.

In yet another embodiment, the present invention provides a method of protecting tissue of a patient during a surgical procedure, wherein the method includes: providing a presurgical skin preparation; providing a free-standing water-absorbing stress-distributing layer comprising a hydrogel, a hydrocolloid, or a combination thereof, wherein the stress-distributing layer has opposite first and second major surfaces; treating the patient's skin with a presurgical skin preparation; adhering the free-standing water-absorbing stress-distributing layer to the patient over the area treated with the presurgical skin preparation; making an incision through the presurgical skin preparation and the stress-distributing layer into the tissue; and retracting the tissue along the incision using a retractor; wherein the presurgical skin preparation and stress-distributing layer undergo stretching and/or compression during retraction.

In addition to methods, the present invention provides kits. One exemplary embodiment of a kit for use during a surgical procedure to protect tissue of a patient includes: a surgical incise drape comprising a flexible polymeric film having opposite first and second major surfaces, a pressure sensitive adhesive disposed on at least a portion of at least one major surface of the film, and a release liner disposed on the pressure sensitive adhesive; and a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof. Typically, the kit includes sterile packaging enclosing the surgical incise drape and stress-distributing layer.

In another embodiment, a kit for use during a surgical procedure to protect tissue of a patient includes: a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof; and a presurgical skin preparation. Typically, the kit includes sterile packaging enclosing the stress-distributing layer and the presurgical skin preparation.

In yet another embodiment, a kit for use during a surgical procedure to protect tissue of a patient includes: a flexible polymeric film having opposite first and second major surfaces, a pressure sensitive adhesive disposed on at least a portion of at least one major surface of the film, and a release liner disposed on the pressure sensitive adhesive; a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof; and a presurgical skin preparation. Typically, the kit includes sterile packaging enclosing the surgical incise drape and stress-distributing layer.

The present invention also provides stress-distributing composites adhered to the skin of a patient. In one embodiment, the stress-distributing composite includes: a presurgical skin preparation on the skin of the patient; and a water-absorbing stress-distributing layer having opposite first and second major surfaces; wherein the water-absorbing stress-distributing layer comprises a hydrogel, a hydrocolloid, or a combination thereof; wherein at least a portion of the stress-distributing layer is at least 1 mm thick between the first and second major surfaces; wherein the water-absorbing stress-distributing layer is adhered to the presurgical skin preparation on the patient's skin. If desired, the composite can include an incise drape adhered to the water-absorbing stress-distributing layer on the patient.

In another embodiment, a stress-distributing composite adhered to the skin of a patient includes: a presurgical skin preparation on the skin of the patient; a surgical incise drape comprising a flexible polymeric film having opposite first and second major surfaces, a pressure sensitive adhesive disposed on at least a portion of at least one major surface of the film; and a water-absorbing stress-distributing layer having opposite first and second major surfaces; wherein the water-absorbing stress-distributing layer comprises a hydrogel, a hydrocolloid, or a combination thereof; wherein at least a portion of the stress-distributing layer is at least 1 mm thick between the first and second major surfaces; wherein the surgical incise drape is adhered to the presurgical skin preparation on the patient's skin by the pressure sensitive adhesive and the water-absorbing stress-distributing layer is attached to the incise drape on the surface opposite the pressure sensitive adhesive.

The term "water-absorbing" in the context of a stress-distributing layer refers to a material (e.g., hydrogel or hydrocolloid) that will absorb at least 10% of its weight in water when in the dry form and immersed in 23° C. deionized water (without a release liner) for 4 hours. Thus, although the water-absorbing layer may include some material that is not water-absorbing, the overall layer is water-absorbing.

The term "hydrogel" as used herein means a polymeric matrix that is capable of absorbing at least 10% water without dissolving or disintegrating. Preferred hydrogels are a hydrophilic crosslinked polymeric matrix.

The term "hydrocolloid" as used here in means a hydrophobic polymeric matrix which has dispersed throughout one or more water-absorbent particulate materials.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a stress-distributing layer comprising a water-absorbing polymer can be interpreted to mean that the stress-distributing layer includes "one or more" water-absorbing materials.

As used herein, the term "or" is generally employed in its sense including "and/or" unless the content clearly dictates otherwise.

The term "and/or" means one or all of the listed elements or a combination of any two or more of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 1 is a cross-section of one embodiment of the invention including a stress-distributing layer disposed on a release liner.

FIGS. 2a and 2b are cross-sections of two embodiments of the invention including a stress-distributing layer disposed on a flexible polymeric film.

FIGS. 3a and 3b are cross-sections of two embodiment of the invention including a stress-distributing layer having a non-uniform thickness.

FIG. 4 is a representation of a kit containing an incise drape and a stress-distributing layer.

FIG. 5b is a photograph of a hydrocolloid dressing (indicated by arrows) applied over the incise drape shown in FIG. 5a.

DETAILED DESCRIPTION OF ILLUSTRATIVE EMBODIMENTS

Figure 5A:
FIG. 5a is a photograph of a patient hip covered with an incise drape.

The present invention is directed to methods and products for protecting tissue affected by the surgical procedure (e.g., the skin and underlying tissue of a patient) during a surgical procedure that involves making an incision in the tissue and retracting the tissue to make a larger opening. Such methods and products use a stress-distributing layer. Although minimally invasive surgical procedures, which typically involve refraction that can result in significant trauma, can benefit from the methods and products of the present invention, a wide variety of surgical procedures can benefit from the present invention. The surgical procedure can be of a wide variety of procedures that involve retraction and significant trauma, particularly when automatic retraction devices (e.g., hand-held refractors, inserted retractors) and/or leverage is required in the refraction process (e.g., for removing bones or portions thereof). Such procedures can be minimally invasive or open, including, for example, transplant surgeries (e.g., liver transplant), cardiovascular surgeries, Caesarian sections, and anteroposterior repair (for colorectal cancer), and hernia repair.

Specifically, the methods and products involve the use of stress-distributing layer in a surgical procedure to protect the tissue (e.g., skin) of a patient. The stress-distributing layer is water-absorbing as a result of it including a hydrogel, a hydrocolloid, or a combination thereof. In the methods of the invention, this stress-distributing layer is adhered to the patient such that it conforms to the shape of the tissue of the patient. To accomplish this, the stress-distributing layer can be an inherently tacky material and directly adhered to the tissue. Alternatively, it can be adhered to the tissue through a pressure sensitive adhesive. Alternatively, the stress-distributing layer can be adhered to an incise drape, which can be adhered to the patient. Whatever method or mechanism is used to adhere the stress-distributing layer to the tissue of a patient, methods of the invention include making an incision through the stress-distributing layer into the tissue, and retracting the tissue, wherein the stress-distributing layer undergoes stretching and/or compression during the retraction. Typically, at least a portion of the stress-distributing layer is positioned between the retractor and the tissue, and preferably, the stress-distributing layer is not torn during retraction. More preferably, the stress-distributing layer adheres sufficiently to the tissue such that retracting does not displace the stress-distributing layer from the patient along the incision while undergoing stretching and/or compression.

In certain embodiments, the methods and products involve the use of a flexible polymeric film, preferably in the form of an incise drape, and a stress-distributing layer. These materials are attached together (either before (by the manufacturer or practitioner) or during the surgical procedure) and adhered to tissue (e.g., skin) during the surgical procedure. Although these materials can be opaque, they are preferably sufficiently clear (transparent or translucent) to allow the practitioner to visualize the underlying tissue through the flexible polymeric film and the stress-distributing layer. Methods of the invention involve making an incision through the flexible polymeric film, the stress-distributing layer if present, and tissue, and retracting the incision to allow the practitioner (e.g., surgeon) better access to the underlying body structures. Typically, at least a portion of the flexible polymeric film (if present) and stress-distributing layer is positioned between the retractor and the tissue and the tissue, flexible polymeric film, and stress-distributing layer are all retracted, wherein retracting stretches and/or compresses the flexible polymeric film and stress-distributing layer.

Although not intending to be limiting, it is believed that the stress-distributing layer absorbs, spreads out, and/or diminishes the force per unit are (pressure) applied by the retractor, thereby reducing pressure on the capillary bed, particularly at skin folds. The reduced pressure also may relieve other potential tissue trauma. For example, it may prevent the tissue from stretching by reinforcing the tissue. This can result in one or more of the following: faster healing; better cosmesis; reduction in site infections; and reduced post surgery pain. It may also facilitate and speed closure by preventing distention of the tissue along the wound edge. Thus, the stress-distributing layers used herein are designed to protect the skin and underlying tissue from the trauma due to high compressive and/or stretching forces during tissue refraction, which occurs in nearly all procedures to some degree.

The stress-distributing layer can be used with or without a flexible polymeric film, although using both is generally preferred. That is, for example, a stress-distributing layer can be applied to the tissue (e.g., skin) of the patient, which is typically first treated with a presurgical skin preparation. Alternatively, a stress-distributing layer can be applied to a flexible polymeric film, such as an incise drape, which is typically first applied to the tissue of the patient after being treated with a presurgical skin preparation. Alternative methods of use of the stress-distributing layer are also envisioned as further described herein.

The stress-distributing layer can be provided as a single layer 10 of a stress-distributing material, which can be disposed on a release liner 12, for example, as shown in FIG. 1. A release liner may be on one or both major surfaces of the stress-distributing layer. The stress-distributing layer may be inherently tacky and/or it may include a layer of a pressure sensitive adhesive thereon.

Alternatively, as shown in FIG. 2a, a flexible polymeric film and stress-distributing layer can be provided as a stress-distributing composite in which the stress-distributing layer 20 is disposed on (e.g., by coating or extruding) a surface of the flexible polymeric film 22. In this embodiment, the flexible polymeric film 22 may or may not include a layer of a pressure sensitive adhesive 24 on the surface of the flexible polymeric film 22 opposite that on which the stress-distributing layer 20 is disposed. The embodiment shown in FIG. 2a would typically be applied to a patient using the pressure sensitive adhesive 24 resulting in the flexible polymeric film being disposed between the tissue of the patient and the stress-distributing layer.

Or, as shown in FIG. 2b, a flexible polymeric film and stress-distributing layer can be provided as a stress-distributing composite in which the stress-distributing layer 20 is disposed on (e.g., by coating or extruding) a surface of the flexible polymeric film 22. In this embodiment, the stress-distributing layer 20 may or may not include a layer of a pressure sensitive adhesive 24 on the surface of the stress-distributing layer 20 opposite that on which the flexible polymeric film 22 is disposed. The embodiment shown in FIG. 2b would typically be applied to a patient using the pressure sensitive adhesive 24 resulting in the stress-distributing layer being disposed between the tissue of the patient and the flexible polymeric film.

The stress-distributing layer and flexible polymeric film of FIGS. 2a and 2b may be attached together directly (without any intervening materials) or through the use of a pressure sensitive adhesive, for example. They may be of the same size, or as shown in FIGS. 2a and 2b, the flexible polymeric film 22 may be larger in area than that of the stress-distributing layer 20. In each of the figures presented herein, the relative sizes (e.g., thicknesses and lengths) of the layers/films are not necessarily in relative proportion.

Although the stress-distributing layer is shown in FIGS. 1, 2a, and 2b as having a uniform thickness (between the two major surfaces), the thickness may vary along the length of the material. For example, as shown in FIGS. 3a and 3b, the stress-distributing layer may be thicker at the center and thinner (e.g., tapered as shown in FIG. 3a) at the edges.

In some embodiments, the flexible polymeric film and stress-distributing layer can be provided as two separate articles in a kit (FIG. 4). For example, a kit 40 can include, within sterile packaging 41, a surgical incise drape including a flexible polymeric film 43, a layer of a pressure sensitive adhesive 44, and a release liner 45, and a stress-distributing layer 46 can include such layer disposed on a release liner 48. Such stress-distributing layer can be a commercially available wound dressing, for example. That is, the stress-distributing layer can be provided in the form of a commercially available wound dressing containing a water-absorbing material in combination with a commercially available surgical incise drape. These two separately provided articles can then be attached together by the practitioner either before surgery or during surgery. This allows for the practitioner to apply the flexible polymeric film (e.g., surgical incise drape) where desired, and then place the stress-distributing layer (e.g., wound dressing) anywhere on the polymeric film.

In some embodiments, the stress-distributing layer and a presurgical skin preparation can be provided as two separate articles in a kit. In other embodiments, the flexible polymeric film, presurgical skin preparation, and stress-distributing layer can be provided as separate articles in a kit. Such kits are typically packaged in sterile packaging.

Thus, when provided for surgeries, the various articles (flexible polymeric film, stress-distributing layer, incise drape, etc.) used herein are sterile. Herein sterilization can be carried out by any means typically used in the medical industry industry (e.g., by sterilizing gas such as ethylene oxide or hydrogen peroxide, by heat, or other radiation techniques such as X-ray, gamma ray, electron beams, etc.).

Again, although a stress-distributing layer can be used alone, it is typically used together with a flexible polymeric film. The flexible polymeric film (e.g., surgical incise drape) is typically disposed between the stress-distributing layer and the tissue (e.g., skin) of the patient for best results. It is envisioned, however, that the stress-distributing layer can be disposed between the flexible polymeric film and the tissue. The latter is less desirable, however, because this could result in gaps between the flexible polymeric film and the tissue, which could result in undesirable fluid collection.

Flexible Polymeric Films

Useful flexible polymeric films are preferably transparent or translucent polymeric material. The material of the flexible films preferably allows for moisture evaporation through the film during prolonged surgeries. Flexible polymeric films of the present invention are typically provided in the form of incise drapes. The flexibility is sufficient for the film to conform to body parts of the patient.

Incise drapes are commonly used in surgical procedures to minimize exposure of the surgical wound to bacterial contamination from bacteria on the patient's skin. Draping of the surgical site provides a sterile work surface and helps minimize the transfer of microorganisms between non-sterile areas and the surgical wound. These measures also may help protect health care professionals from exposure to pathogens in the patient's blood and other body fluids. Incise drapes also may be employed to hold other articles such as fabric drapes securely to the operative site.

For proper functioning of a surgical incise drape, the incise drape is wrinkle-free after it is applied, especially directly at the incision point in order for the practitioner (e.g., surgeon) to be able to make a clean surgical incision. Wrinkles in the drape make it difficult for the practitioner to see through to the skin (transparency or translucency and visibility are desirable, but not required). Furthermore, if the incise drape includes wrinkles, the incise drape may not prevent bacteria on the skin from getting into the wound due to fluid channeling under the drape in these wrinkles maintaining a sterile surface at the point of incision helps prevent surgical wound infections.

The flexible polymeric film of an incise material is usually a clear polymeric film with an adhesive on one side that is covered with a release liner. Examples of suitable incise drapes include those available under the tradenames STERI-DRAPE and IOBAN from 3M Company, St. Paul, Minn. Such drapes are substantially clear (transparent or translucent) and include a flexible film with one major surface coated with a pressure sensitive adhesive that adheres securely to incisional edges (i.e., wound edges), which assists in maintaining the barrier to skin flora. Such drapes conform to the body contours. Other incise drapes are available from suppliers such as T. J. Smith and Nephew Ltd., Medline, and Cardinal, for example. Suitable incise drapes are described, for example, in U.S. Pat. Nos. 4,310,509; 4,323,557; 4,452,845; 4,584,192; 5,803,086; 5,979,450; 5,985,395; 6,939,936; Re. 31,886; and Re. 31,887.

Typically incise drapes are formed from a transparent or translucent flexible polymeric material. The material preferably allows for moisture evaporation through the film during prolonged surgeries. Particularly suitable materials for incise drapes include polyolefins, such as low density polyethylene and particularly metallocene polyethylenes (e.g., that available under the tradename ENGAGE polyethylenes from Dow Chemical Co.), polyurethanes such as polyester or polyether polyurethanes (e.g., that available under the tradename ESTANE thermoplastic polyurethane from B.F. Goodrich, Cleveland, Ohio), polyesters such as polyether polyester (e.g., that available under the tradename HYTREL polyester elastomer from Du Pont Co., Wilmington, Del.), and polyamides such as polyether polyamides (e.g., that available under the tradename PEBAX Resins from ELF Atochem, North America, Inc., Philadelphia, Pa.). Furthermore, the film is flexible, and preferably somewhat elastomeric, to improve conformability when applied to a patient. For these reasons, the preferred films are polyurethanes, polyether polyesters, and polyether polyamides. The film will typically have a thickness of no greater than 200 microns, often no greater than 130 microns, and even more often no greater than 52 microns. The film will typically have a thickness of at least 6 microns, and often at least 13 microns.

In certain embodiments, at least a major portion of at least one surface of the flexible film is coated with a pressure sensitive adhesive. Although the entire length of the flexible film is coated with the adhesive, any major portion may be coated that allows the surgical incise drape to serve its useful function, e.g., the adhesive need not coat the entire width or length of the drape. For example, non-coated portions may be included at any of the edges of the flexible film to assist in removal of the drape from the patient or to assist in attachment of a handle to the film. The adhesive coating the flexible film is preferably a tacky pressure sensitive adhesive at body temperature that will adhere aggressively to the skin. Uniform attachment to the skin surface helps maintain a sterile surgical field. Aggressive adhesives are preferred due to the stress the film is under during surgery as a result of the retraction of the wound (i.e., incision), the warm moist environment, and the abrasion the film may encounter as the surgeon's hands and instruments move in and out of the wound.

Suitable pressure sensitive adhesives are skin compatible and include those described, for example, in U.S. Pat. Nos. 4,310,509, 4,323,557, 6,216,699, and 5,829,422, as well as PCT publication Nos. W0 00/56828 and W0 00/78885. Suitable pressure sensitive adhesives include a polymeric resin composition that can be coatable, for example, by a hot melt process, the components of which are selected to provide the desired adhesive properties of the ultimate adhesive composition. Examples of pressure sensitive adhesive compositions useful in the present invention include, for example, those based on natural rubbers, synthetic rubbers, styrene block copolymers including but not limited to Styrene-Isoprene-Styrene (SIS), styrene-butadiene, styrene-isoprene and derivatives thereof such as those available from Kraton Polymers under the KRATON tradename, polyvinyl ethers, poly (meth)acrylates (including both acrylates and methacrylates), polyolefins such as polyalpha olefins, silicones, and blends or mixtures thereof. Particularly preferred adhesive compositions are based on poly (meth)acrylates (including both acrylates and methacrylates). The polyacrylates may also comprise other vinylic non-acrylate monomers such as but not limited to N-vinyl lactams, (meth)acrylamides, styrene, methylvinyl ether, polystyrene macromers, vinyl acetate, and the like. The pressure sensitive adhesive will typically have a thickness of no greater than 200 microns, often no greater than 150 microns, more often no greater than 100 microns, and even more often no greater than 50 microns. The pressure sensitive adhesive will typically have a thickness of at least 10 microns, often at least 20 microns, and even more often at least 30 microns.

The pressure sensitive adhesive may be made from a formulation of polymers that is inherently tacky. If desired, tackifiers may be added to a base polymeric formulation to form the pressure sensitive adhesive. Useful tackifiers include, for example, rosin ester resins, aromatic hydrocarbon resins, aliphatic hydrocarbon resins, and terpene resins. Other materials can be added for special purposes, including, for example, oils, plasticizers, antioxidants, ultraviolet ("UV") stabilizers, hydrogenated butyl rubber, pigments, dyes, hydrocolloid particles such as those used in bioadhesive compositions and wound dressings disclosed in U.S. Pat. Nos. 5,750,134 and 5,633,010, additional antimicrobial agents, antioxidants, and curing agents.

Some incise drapes, such as that available under the tradename IOBAN, contain an antimicrobial agent, preferably iodophor, in the adhesive. The addition of antimicrobials to the drape adhesive provides the added benefit of helping to further minimize the potential of surgical infections by the maintenance of a bactericidal/bacteriostatic environments against the skin to greatly reduce the number of bacteria. Suitable optional antimicrobial agents are described, for example, in U.S. Pat. No. 5,369,155, at column 12, lines 32-39, which includes iodine and iodophors. For example, such antimicrobial agents that may optionally be incorporated in the pressure sensitive adhesive include alpha-hydroxyacids, such as but not limited to lactic acid, malic acid, citric acid, 2-hydroxybutanoic acid, 3-hydroxybutanoic acid, mandelic acid, gluconic acid, tartaric acid, as well as derivatives thereof (e.g., compounds substituted with hydroxyls, phenyl groups, hydroxyphenyl groups, alkyl groups, halogens, as well as combinations thereof); betahydroxyacids such as salicylic acid; C8-C18 fatty acids; C8-C18 unsaturated fatty acids; C8-C18 alkyl lactylates and their salts; C8-C18 sulfonic acids and there salts; quaternary ammonium surfactants having at least one alkyl chain of at least 8 carbon atoms and/or a benzyl group; parachlorometaxylenol (PCMX); triclosan; hexachlorophene; fatty acid monoesters of glycerin and propylene glycol, such as but not limited to glycerol monolaurate, glycerol monocaprylate, glycerol monocaprate, propylene glycol monolaurate, propylene glycol monocaprylate, propylene glycol monocaprate; phenols; polyquaternary amines, such as but not limited to polyhexamethylene biguanide; chlorhexidine salts; benzethonium halides and derivatives such as methylbenzethonium chlorides; quaternary ammonium silanes having at least one alkyl chain of at least 8 carbon atoms; silver and silver salts, such as but not limited to silver chloride, silver oxide, and silver sulfadiazine; methyl, ethyl, propyl, and butyl parabens; octenidene; compounds that generate hydrogen peroxide such as perborates, complexes of hydrogen peroxide with polyvinylpyrrolidone (e.g., Peroxydone from ISP), natural oils such as tea tree oil, grape fruit seed extract, and the like, as well as combinations thereof.

Drapes typically have a release liner against the adhesive to protect the sterile adhesive surface prior to use. The release liner could be made of a variety of materials such as paper, plastic coated paper, plastic film, woven, non-woven, or knit textiles, as well as film textile laminates. Preferred release liner materials include clear polymeric liners that allow the clinician to see through to the patient and thus accurately place the film. Preferred clear polymeric liners include polyolefins such as polyethylene and polypropylene, or polyester liners, as well as laminates such as polyolefin coated polyester. For products intended for gamma sterilization, use of a paper, polyethylene, polyester, or polyethylene coated polyester liner is preferred.

For those drapes wound onto themselves without release liners, the flexible films are usually treated on the back side with a release coating such as silicone. If used such that the stress-distributing layer is disposed on the back side of the flexible film, no release coating would typically be used, thereby ensuring good adhesion between the film and the stress-distributing layer.

The flexible film may also be treated prior to coating of the pressure sensitive adhesive thereon to enhance the adhesion of the adhesive to the flexible film substrate. Treatments useful for enhancing the adhesion of a pressure sensitive adhesive and/or the stress-distributing layer to the flexible film include chemical priming and corona treatment.

Stress-Distributing Layers

Stress-distributing layers suitable for use in the present invention include water-absorbing materials such as hydrogels, hydrocolloids, or combinations thereof. Such stress-distributing layers can include a high fluid content (as with a hydrogel), or they can be capable of absorbing a high fluid content (as with a hydrocolloid). The stress-distributing layer can be in the form of a free-standing layer (i.e., a layer of sufficient integrity it does not need to be disposed on a flexible polymeric film, for example, although it can optionally be protected by one or more release liners of the type often used on pressure sensitive adhesives), or as a layer attached to (e.g., coated or extruded on) the flexible polymeric film (e.g., that of an incise drape). The stress-distributing layer can be provided as a portion of a separate article (e.g., a water-absorbing layer coated on a film or sandwiched between two films, as in a wound dressing), with opposite first and second major surfaces.

In general, the stress-distributing layers are sufficiently compliant to conform to contours of the body, such as hips or shoulders. Also, the stress-distributing layer has sufficient cohesiveness and integrity such that it does not crumble, or otherwise come apart during use, thereby leaving particulate in the incision site.

Either the stress-distributing layers are inherently tacky, or they are compatible with a pressure sensitive adhesive to provide excellent attachment to the underlying tissue, to skin preparation coatings left in place on the skin to reduce bacterial counts, and/or to the flexible polymeric films (e.g., surgical drapes that are attached directly to the tissue). If a pressure sensitive adhesive is used in combination with the stress-distributing layer (e.g., as a coating on the stress-distributing layer or a film to which the stress-distributing layer is attached), it can be of the same type as that described herein for surgical incise drapes.

Ideally the stress-distributing layer is clear to allow visualization of body landmarks and the site where the incision will be made, although opaque materials can be used. Slight coloration may be added, however, preferably it is slight in order to allow good visualization of the site. The material is also preferably cut easily by a scalpel and allows for penetration through it such that it does not bind the scalpel while creating the incisional opening.

During retraction, the edges of the stress-distributing layer, and the optional flexible polymeric film, preferably roll into the incision while not tearing. More preferably, the stress-distributing layer, does not form a gap or space between it and the underlying tissue and/or the optional flexible polymeric film. That is, preferably, the stress-distributing layer and the flexible polymeric film, if used, are not displaced from the edges of the tissue along the incision (i.e., the incisional edges). These gaps or spaces allow irrigation or body fluids to collect which may increase the potential for infection.

Stress-distributing layers suitable for incisional stress redistribution preferably include those materials that have no biocompatibility issues with the body. Typical biocompatibility testing includes the determination of cytotoxicity, sensitization, irritation, genotoxicity, acute system toxicity, hemocompatibility, and subchronic toxicity among other tests. These tests insure that the materials used in the product are not injurious to the patient, that the materials do not cause negative responses when in contact with body cells and that any material which leaches from the product due to surgical irrigation or body fluid contact do not cause systemic toxic effects.

The stress-distributing layers may be solid or porous. Porosity may be desirable to allow moisture to evaporate through the material. Porosity can be imparted by, for example, making the stress distributing material an open cell foam. Alternatively, closed cell foams and solid layers of stress-distributing materials may have through-holes in the material. For example, some materials can be extruded onto a belt having pins from which it is subsequently removed to leave holes. Alternatively, holes may be punched, drilled, burned (e.g., by a laser), or otherwise formed. The holes may extend through the adhesive coating or not.

Suitable stress-distributing layers useful in the methods and products of the present invention include water-absorbing polymers—hydrogels, hydrocolloids, or combinations thereof. The term "water-absorbing" in the context of a stress-distributing layer refers to a layer (including hydrogel and/or hydrocolloidal polymers) that will absorb at least 10% of its weight in water when in the dry form and immersed in 23° C. deionized water (without a release liner) for 4 hours. That is, although the stress-distributing layer may be applied in a hydrated form, when it is in a non-hydrated or dry form, it will absorb at least 10% of its weight in water.

Hydrogels are typically applied in their hydrated form to allow for sufficient conformability. Hydrocolloids are typically applied in their dry form as they are sufficiently conformable without being in their hydrated form, although they can also be applied in a hydrated form. In some instances, a hydrocolloid may need to be are warmed to make it more compliant. Preferred materials are the hydrocolloids typically because they generally have more integrity than the hydrogels.

Suitable hydrogel materials are discussed in "Advanced Drug Delivery Reviews," 43 (2002), 3-12 and include both natural and synthetic polymers and derivatives. Natural components include hyaluronic acid, alginic acid, pectin, carrageenan, chondroitin sulfate, dextran sulfate, chitosan, polylysine, collagen, fibrin, carboxymethyl chitin, dextran, agarose, lecithin, polysaccharides, and polysaccharide-based material, s among others. Synthetic polymers and components include acrylate and methacrylate-based hydrogels, such as poly(2-hydroxyethyl methacrylate) (poly-HEMA), HEMA-methacrylic acid copolymers, HEMA-2-(N,N-diethylamino)ethyl methacrylate (DEAEMA) copolymers, HEMA-methyl acrylate, HEMA-butyl acrylate, HEMA-methyl methacrylate, HEMA-N-vinyl-2-pyrrolidone; acrylamide-based hydrogels, such as polyacrylamide, poly(N-isopropyl acrylamide) (PNIPAAm)-acrylic acid, acrylamide-N-vinyl-2-pyrrolidone copolymers, acrylamide-acrylic acid-acrylonitrile terpolymers, N-(2-hydroxypropyl) methacrylamide; silicone polymers; and 2-acrylamido-2-methanepropane sulfonic acid (AMPS); and the like. A considerable number of other monomers may be reacted to these and other hydrophilic monomers to modify mechanical properties such as tensile and elongation, or adjust the balance of hydrophilicity/hydrophobicity. Combinations of hydrogel materials to form interpenetrating networks or combining natural and synthetic polymers are also possible. A variety of crosslinking mechanisms such as copolymerization with di- and tri-functional monomers, radiation crosslinking with e-beam or gamma radiation, or the use of metal salts to crosslink charged hydrogels or water soluble polymers such as poly(vinyl alcohol) is possible.

Examples of suitable hydrogel films are disclosed, for example, in U.S. Pat. No. 477,943. Examples of water-absorbing polymers suitable to form stress-distributing layers include, for example, hydrogels based on polyurethane (such as those described in U.S. Pat. Nos. 3,822,238; 3,975,350; and 4,454,309), or polyacrylonitrile (such as those described in U.S. Pat. Nos. 4,420,589; 4,369,294; and 4,379,874).

Examples of suitable hydrocolloid films include hydrocolloid adhesive compositions that are often used as wound dressings. Typically, these compositions comprise a blend of a polymer matrix, such as a rubbery elastomer like polyisobutylene, in combination with one or more water-soluble or water-swellable hydrocolloids, such as a dry powdered mixture of pectin, gelatin and carboxymethylcellulose.

A hydrocolloid composition can be used by applying it directly to the flexible polymeric film prior to surgery (e.g., as in a coating or extruding method during manufacturing). Alternatively, it can be provided in a form that allows it to be attached to the flexible polymeric film during surgery. For example, it could be provided as a free-standing layer with one or more release liners attached thereto, or it could be coated on at least one surface of a water-insoluble film to form an article similar to commercially available wound dressings.

Commercially available examples of hydrocolloid wound dressings that can be used in methods of the present invention to provide the stress-distributing layer include those available under the tradenames DUODERM and DUODERM EXTRA-THIN wound dressings (products of Convatec, Squibb and Sons, Inc., Princeton, N.J.; believed to be a KRATON-based composition); TEGASORB wound dressing (a product of 3M Company, St. Paul, Minn.; a polyisobutylene-based composition); RESTORE wound dressing (a product of Hollister, Inc., Libertyville, Ill.; believed to be an ethylene vinyl acetate (EVA)-based composition); and COMFEEL wound dressing (a product of Coloplast International, Espergaerde, Denmark; believed to be a KRATON-based composition). Other suitable hydrocolloids include those disclosed in U.S. Pat. Nos. 4,231,369; 4,477,325; 4,551,490; 4,738,257 and 5,633,010.

Depending on the material and its properties (e.g., modulus), the thickness of the stress-distributing layer may vary. The material may also be crosslinked (e.g., by chemical or radiation means), which can affect the softness or stiffness of the material.

The material of the stress-distributing layer may be inherently tacky. The elasticity of a pressure sensitive adhesive may be utilized by coating a thick film form to prepare a stress-distributing layer. Hot melt, solution, emulsion, or radiation curable techniques are exemplary coating methods. Hot melt or radiation curable systems are particularly useful in that drying of a solvent is not necessary to form the thick layers. In some examples, the delivery system for the stress-distributing layer is a simple release liner to protect the tacky surface. Alternatively, a thin, adhesive-coated polymeric backing extended beyond the edges of the stress-distributing layer can be used to form a border that will adhere, for example, to the skin and/or flexible polymeric film (e.g., incise drape) and provide a barrier to outside contamination.

The top surface of the stress-distributing material preferably has a matte finish to prevent reflection and glare which may be distracting to the surgeon and nurses.

In some embodiments, the stress-distributing layer can contain an antimicrobial agent. The addition of antimicrobials to the stress-distributing layer provides the added benefit of helping to further minimize the potential of surgical infections by the maintenance of bactericidal/bacteriostatic environments against the skin to greatly reduce the number of bacteria. Suitable optional antimicrobial agents are described, for example, in U.S. Pat. No. 5,369,155, at column 12, lines 32-39, which includes iodine and iodophors. For example, such antimicrobial agents that may optionally be incorporated in the pressure sensitive adhesive include alpha-hydroxyacids, such as but not limited to lactic acid, malic acid, citric acid, 2-hydroxybutanoic acid, 3-hydroxybutanoic acid, mandelic acid, gluconic acid, tartaric acid, as well as derivatives thereof (e.g., compounds substituted with hydroxyls, phenyl groups, hydroxyphenyl groups, alkyl groups, halogens, as well as combinations thereof); betahydroxyacids such as salicylic acid; C8-C18 fatty acids; C8-C18 unsaturated fatty acids; C8-C18 alkyl lactylates and their salts; C8-C18 sulfonic acids and there salts; quaternary ammonium surfactants having at least one alkyl chain of at least 8 carbon atoms and/or a benzyl group; parachlorometaxylenol (PCMX); triclosan; hexachlorophene; fatty acid monoesters of glycerin and propylene glycol, such as but not limited to glycerol monolaurate, glycerol monocaprylate, glycerol monocaprate, propylene glycol monolaurate, propylene glycol monocaprylate, propylene glycol monocaprate; phenols; polyquaternary amines, such as but not limited to polyhexamethylene biguanide; chlorhexidine salts; benzethonium halides and derivatives such as methylbenzethonium chlorides; quaternary ammonium silanes having at least one alkyl chain of at least 8 carbon atoms; silver and silver salts, such as but not limited to silver chloride, silver oxide, and silver sulfadiazine; methyl, ethyl, propyl, and butyl parabens; octenidene; compounds that generate hydrogen peroxide such as perborates, complexes of hydrogen peroxide with polyvinylpyrrolidone (e.g., Peroxydone from ISP), natural oils such as tea tree oil, grape fruit seed extract, and the like, as well as combinations thereof.

Alternatively, the stress-distributing layer and the flexible polymeric film can be provided as a composite article. For example, U.S. Pat. No. 5,369,155 discloses a composite of a gel of swollen hydrocolloid particles dispersed in a pressure sensitive adhesive matrix. The gel-adhesive composite may be coated on the flexible polymeric film and provided as a composite article and used in methods of the present invention. Also, International Publication Nos. WO2009/088757 and WO2009/091682 disclose adhesive hydrogel island dressings that could be used as a stress-distributing layer in methods of the present invention.

Depending on the material and its properties (e.g., modulus), the thickness of the stress-distributing layer may vary. The thickness of the stress-distributing layer, which has opposite first and second major surfaces, is typically at least 1 millimeter (mm), preferably at least 2 mm, between the first and second major surfaces. A stress-distributing layer of greater than 2 mm is preferred at least because this thickness is better to distribute the stresses imposed by retraction as a result of stretching and/or compression, for example. If the stress-distributing layer is too thick, the practitioner may not be able to feel the underlying anatomy (e.g., bony prominences) for effective placement of the incision. Also, as the thickness of the stress-distributing layer increases, its conformability over curved body surfaces typically decreases. The thickness of the stress-distributing layer is typically no more than 10 mm, often no more than 8 mm, and even more often no more than 5 mm. An exemplary range of thicknesses is 3 mm to 5 mm. Variations in size of incision, the anatomy at the incision site, the size of the retractors, and the desired surgical procedure may require stress-distributing layers of different thicknesses, which can be determined by the practitioner.

The size of the stress-distributing layer may be of a wide variety of sizes depending on the size of the incision to be made. A typical stress-distributing layer is at least 2 cm longer on each end than the desired length of the incision. A typical stress-distributing layer is at least 3 cm, and often no more than 4 cm, wide on each side of the incision (making a typical stress-distributing layer 6 cm to 8 cm wide). Larger layers can be used if desired, however, such layers are typically wasteful and can be harder to apply.

The thickness of the stress-distributing layer is typically uniform throughout. It can also be contoured or non-uniform, however, such that the thickness may vary throughout the material for desired effect (see, e.g., FIGS. 3a and 3b). For example, it may be thicker in and around the area for the incision (e.g., at the center of the material) and thinner over the remainder of the area (e.g., tapered at the edges of the material), which can result in more conformability at the edges. A tapered construction (as shown in FIG. 3a) may be desired in certain embodiments, particularly where the flexible polymeric material overlies the stress-distributing layer, as the thinner edges result in less of a step at the edges.

Stress-distributing layers may have a release liner against the stress-distributing material to protect the surface prior to use. The release liner could be made of a variety of materials such as paper, plastic coated paper, plastic film, woven, non-woven, or knit textiles, as well as film textile laminates. Preferred release liner materials include clear polymeric liners that allow the clinician to see through to the patient and thus accurately place the film. Preferred clear polymeric liners include polyolefins such as polyethylene and polypropylene, or polyester liners, as well as laminates such as polyolefin coated polyester. For products intended for gamma sterilization, use of a paper, polyethylene, polyester, or polyethylene coated polyester liner is preferred.

Presurgical Skin Preparations

Presurgical skin preparations can be of a variety of well-known types. As used herein, a presurgical skin preparation includes antiseptic skin preparations, antiseptic skin preparations having polymeric film formers, and film forming preparations useful as microbial sealants or barriers. They are described in a number of patents including, U.S. Pat. Nos. 4,584,192; 4,542,012; 7,459,167; and 7,030,203, as well as U.S. Pat. Publication Nos. 2008/0046004 and 2007/0147947.

Methods of Use

Methods of the present invention involve protecting tissue during a surgical procedure and providing, for example, improved cosmesis of the healed incision. Typically the methods described herein include treating the tissue of the patient, e.g., the skin, with a presurgical skin preparation.

Figure 5B:
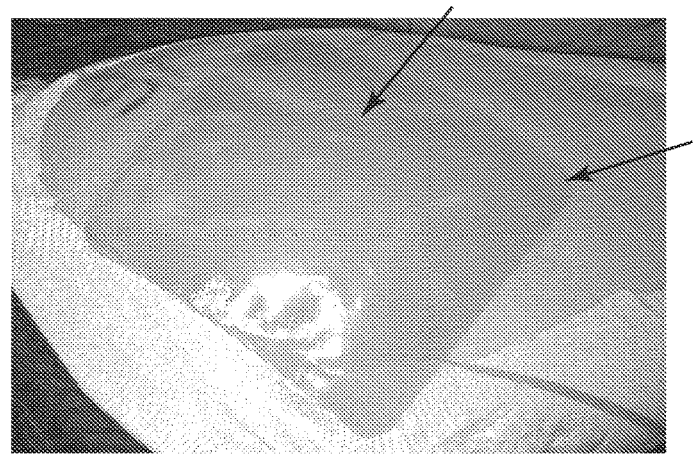
Figure 5C:
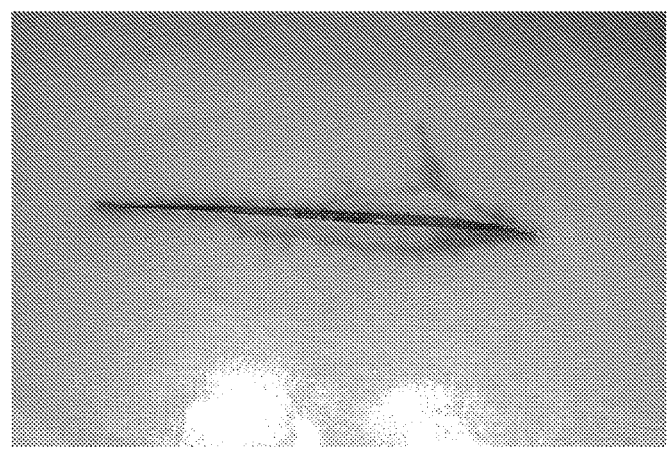
FIG. 5c is a photograph of an incision made into the tissue of the patient's hip through the incise drape and hydrocolloid dressing shown in FIG. 5b.

In certain embodiments, the methods include: applying an incise drape to a patient (e.g., as shown in FIG. 5a, where a patient hip is covered with an IOBAN incise drape, available from 3M Co.) over a presurgical skin preparation followed by applying a stress-distributing layer over the incise drape (e.g., as shown in FIG. 5b, where a hydrocolloid dressing is applied over the incise drape shown in FIG. 5a); or applying the stress-distributing layer to the drape and then applying the composite to the patient; or applying the stress-distributing layer to the tissue (e.g., skin) over a presurgical skin preparation followed by applying an incise drape over the stress-distributing layer; or applying a stress-distributing layer over a presurgical skin preparation such as DuraPrep (without the use of an incise drape); or applying a stress-distributing layer over a presurgical polymeric barrier film such as that available under the trade designation INTEGUSEAL (a cyanoacrylate applied directly to skin in place of an incise) from Kimberly Clark. The methods of the present invention involve making an incision through such coverings (e.g., an incision through an incise drape and hydrocolloid dressing into the tissue of the patient hip as shown in FIG. 5c) and retracting the incised tissue and the coverings.

In certain embodiments, the present invention provides a method of protecting tissue of a patient during a surgical procedure, wherein the method includes: providing a presurgical skin preparation; providing a free-standing water-absorbing stress-distributing layer comprising a hydrogel, a hydrocolloid, or a combination thereof, wherein the stress-distributing layer has opposite first and second major surfaces; treating the patient's skin with a presurgical skin preparation; adhering the free-standing stress-distributing layer to the patient over the area treated with the presurgical skin preparation; making an incision through the presurgical skin preparation and the stress-distributing layer into the tissue; and retracting the tissue along the incision using a retractor; wherein the presurgical skin preparation and stress-distributing layer undergo stretching and/or compression during retraction. In certain embodiments, the method further includes adhering an incise drape to the patient over the area treated with the presurgical skin preparation before or after adhering the free-standing water-absorbing stress-distributing layer to the patient. If "after," the incise drape is adhered to the stress-distributing layer, which is adhered to the patient's skin over the presurgical skin preparation. If "before," the stress-distributing layer is adhered to the incise drape, which is adhered to the patient's skin over the presurgical skin preparation.

In certain embodiments, methods of the invention include: providing a water-absorbing stress-distributing layer comprising a hydrogel, a hydrocolloid, or a combination thereof; wherein the stress-distributing layer has opposite first and second major surfaces and at least a portion of the stress-distributing layer is greater than 2 mm thick between the first and second major surfaces; adhering the stress-distributing layer to the patient such that it conforms to the shape of the tissue of the patient; making an incision through the stress-distributing layer into the tissue; and retracting the tissue along the incision using a retractor; wherein the stress-distributing layer undergoes stretching and/or compression during retraction. In certain embodiments, at least one of the major surfaces of the stress-distributing layer is attached to a flexible polymeric film to form a stress-distributing composite; adhering the stress-distributing layer comprises adhering the stress-distributing composite to the patient such that the stress-distributing composite conforms to the shape of the tissue of the patient; and making an incision comprises making an incision through the stress-distributing composite into the tissue.

The methods described above can use a stress-distributing layer alone or it can be used with a flexible polymeric film such as a surgical incise drape. In this embodiment, the method further includes: providing a surgical incise drape comprising a flexible polymeric film having opposite first and second major surfaces, and a layer of a pressure sensitive adhesive disposed on at least a portion of one major surface; adhering the surgical incise drape to the patient; and attaching the stress-distributing layer to the incise drape; wherein making an incision comprises making an incision through the stress-reducing material and the surgical incise drape into the tissue. In an alternative embodiment, the method further includes: providing a surgical incise drape comprising a flexible polymeric film having opposite first and second major surfaces, and a layer of a pressure sensitive adhesive disposed on at least a portion of one major surface; adhering the stress-distributing layer to the patient; and adhering the surgical incise drape to the stress-distributing layer; wherein making an incision comprises making an incision through the stress-reducing material and the surgical incise drape into the tissue.

Preferred methods of the present invention for protecting tissue of a patient during a surgical procedure involve the use of a stress-distributing layer and a flexible polymeric film. Such methods involve: providing a flexible polymeric film having opposite first and second major surfaces; providing a water-absorbing stress-distributing layer comprising a hydrogel, a hydrocolloid, or a combination thereof; wherein the stress-distributing layer has opposite first and second major surfaces and at least a portion of the stress-distributing layer is at least 1 mm thick between the first and second major surfaces; placing the flexible polymeric film and the stress-distributing layer in contact with one another so that the flexible polymeric film and the stress-distributing layer are attached together to form a stress-distributing composite, and the stress-distributing composite is adhered to the patient such that the stress-distributing composite conforms to the shape of the tissue of the patient; making an incision through the stress-distributing composite into the tissue; and retracting the tissue along the incision using a retractor; wherein the stress-distributing composite undergoes stretching and/or compression during retraction.

In one embodiment of such method, placing the flexible polymeric film and the stress-distributing layer in contact with one another on the patient includes forming a stress-distributing composite comprising the stress-distributing layer and the flexible polymeric film, optionally with a pressure sensitive adhesive between, and placing the stress-distributing composite on the patient and adhering the stress-distributing composite thereto. The flexible polymeric film and the stress-distributing layer can be attached together to form a stress-distributing composite before the surgical procedure (for example, by a manufacturer).

In another embodiment of such method, placing the flexible polymeric film and the stress-distributing layer in contact with one another on the patient includes placing one of the flexible polymeric film and the stress-distributing layer in contact with the patient before the flexible polymeric film and the stress reducing material are attached together to form the stress-distributing composite. For example, placing the flexible polymeric film and the stress-distributing layer in contact with one another on the patient includes placing the stress-distributing layer on the patient and adhering it thereto, and subsequently placing the flexible polymeric film on the stress-distributing layer to form the stress-distributing composite. Alternatively, placing the flexible polymeric film and the stress-distributing layer in contact with one another on the patient includes placing the flexible polymeric film on the patient and adhering it thereto, and subsequently placing the stress-distributing layer on the flexible polymeric film to form the stress-distributing composite.

The stress-distributing layer and the optional flexible polymeric film preferably do not tear during retraction of the tissue. More preferably, the stress-distributing layer, and the optional flexible polymeric film, adheres sufficiently to the tissue such that the refraction does not displace the stress-distributing layer from the patient along the edges of the incision.

Preferably, the flexible polymeric film and stress-distributing layers, and any optional pressure sensitive adhesives are sufficiently clear (either translucent or transparent) to allow the practitioner to visualize the tissue through the flexible polymeric film and the stress-distributing layer. This allows the practitioner to better see the underlying tissue to be incised, particularly if the practitioner marks the tissue at the desired location. If desired, the flexible polymeric film and/or the stress-distributing layer can include a visual grid (e.g., with 1-cm squares) to assist the practitioner in making incisions and/or sutures.

The flexible polymeric film is preferably provided as a surgical incise drape. In many embodiments, the flexible polymeric film, the stress-distributing layer, or both comprises a pressure sensitive adhesive on at least a portion of at least one major surface thereof. This pressure sensitive adhesive typically provides the mode of attachment between the flexible polymeric film and the stress-distributing layer.

In certain embodiments, the flexible polymeric film is provided as an incise drape having a first pressure sensitive adhesive on at least one major surface of the film. In certain embodiments, the stress-distributing layer comprises a second pressure sensitive adhesive on at least one major surface thereof. In certain embodiments, if two such pressure sensitive adhesives are used together (for example, in a stress-distributing composite article), the first and second pressure sensitive adhesives are selected such that, preferably, the incise drape and the stress-distributing layer remain adhered together and the stress-distributing composite adhered securely to the edges of the incision during the surgical procedure.

In one exemplary embodiment using a surgical incise drape, a method of the invention includes: providing a surgical incise drape comprising a flexible polymeric film having opposite first and second major surfaces and a pressure sensitive adhesive on at least a portion of at least one major surface thereof; providing a free-standing water-absorbing stress-distributing layer comprising a hydrogel, a hydrocolloid, or a combination thereof; wherein the stress-distributing layer has opposite first and second major surfaces; adhering the surgical incise drape to the patient; adhering the free-standing stress-distributing layer to the surgical incise drape; making an incision through the incise drape and the stress-distributing layer into the tissue; and refracting the tissue along the incision using a retractor; wherein the surgical incise drape and stress-distributing layer undergo stretching and/or compression during refraction. Preferably, the retracting does not displace the surgical incise drape and stress-distributing layer from the patient along the incision while undergoing stretching and/or compression during retraction.

In certain embodiments, the stress-distributing layer can be provided as multiple layers. For example, in one embodiment, the stress-distributing layer can be folded over on itself and applied as a double layer. That is, when adhering a free-standing stress-distributing layer, for example, to a surgical incise drape, the practitioner can form a double stress-distributing layer (e.g., by folding it) and adhere the two layers to the surgical incise drape.

The present invention also provides products, in particular kits that include the stress-distributing layer and the flexible polymeric film. For example, a kit can include: a surgical incise drape comprising a flexible polymeric film having opposite first and second major surfaces, a pressure sensitive adhesive disposed on at least a portion of at least one major surface of the film, and a release liner disposed on the pressure sensitive adhesive; a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof; and sterile packaging enclosing the surgical incise drape and stress-distributing layer. Another kit includes: a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof; a presurgical skin preparation; and sterile packaging enclosing the stress-distributing layer and the presurgical skin preparation. Yet another kit includes: a flexible polymeric film having opposite first and second major surfaces, a pressure sensitive adhesive disposed on at least a portion of at least one major surface of the film, and a release liner disposed on the pressure sensitive adhesive; a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof; a presurgical skin preparation; and sterile packaging enclosing the surgical incise drape and stress-distributing layer. In each of these kits, at least a portion of the stress-distributing layer is preferably at least 1 mm thick between the first and second major surfaces.

The present invention also provides stress-distributing composites adhered to the skin of a patient. In one such embodiment, the stress-distributing composite includes: a presurgical skin preparation on the skin of the patient; and a water-absorbing stress-distributing layer having opposite first and second major surfaces; wherein the water-absorbing stress-distributing layer comprises a hydrogel, a hydrocolloid, or a combination thereof; wherein at least a portion of the stress-distributing layer is at least 1 mm thick between the first and second major surfaces; wherein the water-absorbing stress-distributing layer is adhered to the presurgical skin preparation on the patient's skin. The stress-distributing composite can further include an incise drape adhered to the water-absorbing stress-distributing layer.

In another embodiment, the present invention provides a stress-distributing composite adhered to the skin of a patient, the stress-absorbing composite including: a presurgical skin preparation on the skin of the patient; a surgical incise drape comprising a flexible polymeric film having opposite first and second major surfaces, a pressure sensitive adhesive disposed on at least a portion of at least one major surface of the film; and a water-absorbing stress-distributing layer having opposite first and second major surfaces; wherein the water-absorbing stress-distributing layer comprises a hydrogel, a hydrocolloid, or a combination thereof; wherein at least a portion of the stress-distributing layer is at least 1 mm thick between the first and second major surfaces; wherein the surgical incise drape is adhered to the presurgical skin preparation on the patient's skin by the pressure sensitive adhesive and the water-absorbing stress-distributing layer is attached to the incise drape on the surface opposite the pressure sensitive adhesive.

EXEMPLARY EMBODIMENTS

1. A method of protecting tissue of a patient during a surgical procedure, the method comprising:
providing a water-absorbing stress-distributing layer comprising a hydrogel, a hydrocolloid, or a combination thereof; wherein the stress-distributing layer has opposite first and second major surfaces and at least a portion of the stress-distributing layer is greater than 2 mm thick between the first and second major surfaces;
adhering the stress-distributing layer to the patient such that it conforms to the shape of the tissue of the patient;
making an incision through the stress-distributing layer into the tissue; and
retracting the tissue along the incision using a retractor;
wherein the stress-distributing layer undergoes stretching and/or compression during retraction.

2. The method of embodiment 1 wherein at least one of the major surfaces of the stress-distributing layer is attached to a flexible polymeric film to form a stress-distributing composite, adhering the stress-distributing layer comprises adhering the stress-distributing composite to the patient such that the stress-distributing composite conforms to the shape of the tissue of the patient, and making an incision comprises making an incision through the stress-distributing composite into the tissue.

3. The method of embodiment 1 further comprising:
providing a surgical incise drape comprising a flexible polymeric film having opposite first and second major surfaces, and a layer of a pressure sensitive adhesive disposed on at least a portion of one major surface;
adhering the surgical incise drape to the patient; and
attaching the stress-distributing layer to the incise drape;
wherein making an incision comprises making an incision through the stress-reducing material and the surgical incise drape into the tissue.

4. The method of embodiment 1 further comprising:
providing a surgical incise drape comprising a flexible polymeric film having opposite first and second major surfaces, and a layer of a pressure sensitive adhesive disposed on at least a portion of one major surface;
adhering the stress-distributing layer to the patient; and
adhering the surgical incise drape to the stress-distributing layer;
wherein making an incision comprises making an incision through the stress-reducing material and the surgical incise drape into the tissue.

5. The method of any one of the preceding embodiments wherein the retracting does not displace the stress-distributing layer from the patient along the incision while undergoing stretching and/or compression during retraction.

6. A method of protecting tissue of a patient during a surgical procedure, the method comprising:
providing a flexible polymeric film having opposite first and second major surfaces;
providing a water-absorbing stress-distributing layer comprising a hydrogel, a hydrocolloid, or a combination thereof; wherein the stress-distributing layer has opposite first and second major surfaces and at least a portion of the stress-distributing layer is at least 1 mm thick between the first and second major surfaces;
placing the flexible polymeric film and the stress-distributing layer in contact with one another so that the flexible polymeric film and the stress-distributing layer are attached together to form a stress-distributing composite, and the stress-distributing composite is adhered to the patient such that the stress-distributing composite conforms to the shape of the tissue of the patient;

making an incision through the stress-distributing composite into the tissue; and retracting the tissue along the incision using a retractor;

wherein the stress-distributing composite undergoes stretching and/or compression during retraction.

7. The method of embodiment 6 wherein placing the flexible polymeric film and the stress-distributing layer in contact with one another on the patient comprises forming a stress-distributing composite comprising the stress-distributing layer and the flexible polymeric film, optionally with a pressure sensitive adhesive between, and placing the stress-distributing composite on the patient and adhering the stress-distributing composite thereto.

8. The method of embodiment 7 wherein the flexible polymeric film and the stress-distributing layer are attached together to form a stress-distributing composite before the surgical procedure.

9. The method of embodiment 6 wherein placing the flexible polymeric film and the stress-distributing layer in contact with one another on the patient comprises placing one of the flexible polymeric film and the stress-distributing layer in contact with the patient before the flexible polymeric film and the stress reducing material are attached together to form the stress-distributing composite.

10. The method of embodiment 9 wherein placing the flexible polymeric film and the stress-distributing layer in contact with one another on the patient comprises placing the stress-distributing layer on the patient and adhering it thereto, and subsequently placing the flexible polymeric film on the stress-distributing layer to form the stress-distributing composite.

11. The method of embodiment 9 wherein placing the flexible polymeric film and the stress-distributing layer in contact with one another on the patient comprises placing the flexible polymeric film on the patient and adhering it thereto, and subsequently placing the stress-distributing layer on the flexible polymeric film to form the stress-distributing composite.

12. The method of any one of embodiments 6 through 11 wherein the flexible polymeric film is provided as a surgical incise drape.

13. The method of any one of embodiments 6 through 11 wherein at least a portion of the stress-distributing layer has a thickness of greater than 2 mm between the first and second major surfaces.

14. The method of any one of embodiments 6 through 13 wherein the flexible polymeric film, the stress-distributing layer, or both comprises a pressure sensitive adhesive disposed on at least a portion of at least one major surface thereof.

15. The method of any one of the preceding embodiments further comprising visualizing the tissue through the stress-distributing layer prior to making the incision.

16. The method of any one of the preceding embodiments wherein the thickness of the stress-distributing layer is uniform.

17. The method of any one of the preceding embodiments wherein the stress-distributing layer is inherently tacky.

18. A method of protecting tissue of a patient during a surgical procedure, the method comprising:

providing a surgical incise drape comprising a flexible polymeric film having opposite first and second major surfaces and a pressure sensitive adhesive on at least a portion of at least one major surface thereof;

providing a free-standing water-absorbing stress-distributing layer comprising a hydrogel, a hydrocolloid, or a combination thereof; wherein the stress-distributing layer has opposite first and second major surfaces;

adhering the surgical incise drape to the patient;

adhering the free-standing stress-distributing layer to the surgical incise drape;

making an incision through the incise drape and the stress-distributing layer into the tissue; and retracting the tissue along the incision using a retractor;

wherein the surgical incise drape and stress-distributing layer undergo stretching and/or compression during retraction.

19. The method of embodiment 18 wherein adhering the stress-distributing layer to the surgical incise drape comprises adhering a double stress-distributing layer to the surgical incise drape.

20. The method of embodiment 18 or embodiment 19 wherein the retracting does not displace the surgical incise drape and stress-distributing layer from the patient along the incision while undergoing stretching and/or compression during retraction.

21. The method of any one of the preceding embodiments wherein the water-absorbing stress-distributing layer comprises a hydrocolloid.

22. The method of any one of the preceding embodiments wherein the water-absorbing stress-distributing layer is porous.

23. The method of any one of the preceding embodiments wherein the water-absorbing stress-distributing layer has a matte finish.

24. The method of any one of the preceding embodiments wherein the tissue of the patient is initially treated with a presurgical skin preparation.

25. The method of any one of the preceding embodiments wherein the tissue of the patient is initially treated with a barrier film.

26. A method of protecting tissue of a patient during a surgical procedure, the method comprising:

providing a presurgical skin preparation;

providing a free-standing water-absorbing stress-distributing layer comprising a hydrogel, a hydrocolloid, or a combination thereof, wherein the stress-distributing layer has opposite first and second major surfaces;

treating the patient's skin with a presurgical skin preparation;

adhering the free-standing water-absorbing stress-distributing layer to the patient over the area treated with the presurgical skin preparation;

making an incision through the presurgical skin preparation and the stress-distributing layer into the tissue; and retracting the tissue along the incision using a retractor;

wherein the presurgical skin preparation and stress-distributing layer undergo stretching and/or compression during retraction.

27. The method of embodiment 26 further comprising adhering an incise drape to the patient over the area treated with the presurgical skin preparation before or after adhering the free-standing water-absorbing stress-distributing layer to the patient.

28. The method of any one of the preceding embodiments wherein the surgical procedure is a minimally invasive or open surgical procedure.

29. The method of any one of the preceding embodiments wherein the surgical procedure is an open surgical procedure.

30. A kit for use during a surgical procedure to protect tissue of a patient, the kit comprising:
a surgical incise drape comprising a flexible polymeric film having opposite first and second major surfaces, a pressure sensitive adhesive disposed on at least a portion of at least one major surface of the film, and a release liner disposed on the pressure sensitive adhesive;
a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof; and
sterile packaging enclosing the surgical incise drape and stress-distributing layer.
31. A kit for use during a surgical procedure to protect tissue of a patient, the kit comprising:
a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof;
a presurgical skin preparation; and
sterile packaging enclosing the stress-distributing layer and the presurgical skin preparation.
32. A kit for use during a surgical procedure to protect tissue of a patient, the kit comprising:
a flexible polymeric film having opposite first and second major surfaces, a pressure sensitive adhesive disposed on at least a portion of at least one major surface of the film, and a release liner disposed on the pressure sensitive adhesive;
a water-absorbing stress-distributing layer having opposite first and second major surfaces, and a release liner disposed on at least one of the surfaces; wherein the water-absorbing stress-distributing layer comprises a hydrogel, a hydrocolloid, or a combination thereof;
a presurgical skin preparation; and
sterile packaging enclosing the surgical incise drape and stress-distributing layer.
33. The kit of any one of embodiments 30 through 302 wherein at least a portion of the stress-distributing layer is at least 1 mm thick between the first and second major surfaces.
34. A stress-distributing composite adhered to the skin of a patient, the stress-distributing composite comprising:
a presurgical skin preparation on the skin of the patient; and
a water-absorbing stress-distributing layer having opposite first and second major surfaces; wherein the water-absorbing stress-distributing layer comprises a hydrogel, a hydrocolloid, or a combination thereof; wherein at least a portion of the stress-distributing layer is at least 1 mm thick between the first and second major surfaces;
wherein the water-absorbing stress-distributing layer is adhered to the presurgical skin preparation on the patient's skin.
35. The stress-distributing composite of embodiment 34 further comprising an incise drape adhered to the water-absorbing stress-distributing layer.
36. A stress-distributing composite adhered to the skin of a patient, the stress-absorbing composite comprising:
a presurgical skin preparation on the skin of the patient;
a surgical incise drape comprising a flexible polymeric film having opposite first and second major surfaces, a pressure sensitive adhesive disposed on at least a portion of at least one major surface of the film; and
a water-absorbing stress-distributing layer having opposite first and second major surfaces; wherein the water-absorbing stress-distributing layer comprises a hydrogel, a hydrocolloid, or a combination thereof; wherein at least a portion of the stress-distributing layer is at least 1 mm thick between the first and second major surfaces;
wherein the surgical incise drape is adhered to the pre-surgical skin preparation on the patient's skin by the pressure sensitive adhesive and the water-absorbing stress-distributing layer is attached to the incise drape on the surface opposite the pressure sensitive adhesive.

EXAMPLES

Objects and advantages of this invention are further illustrated by the following examples, but the particular materials and amounts thereof recited in these examples, as well as other conditions and details, should not be construed to unduly limit this invention.

Example 1 (Comparative)

Figure 6:
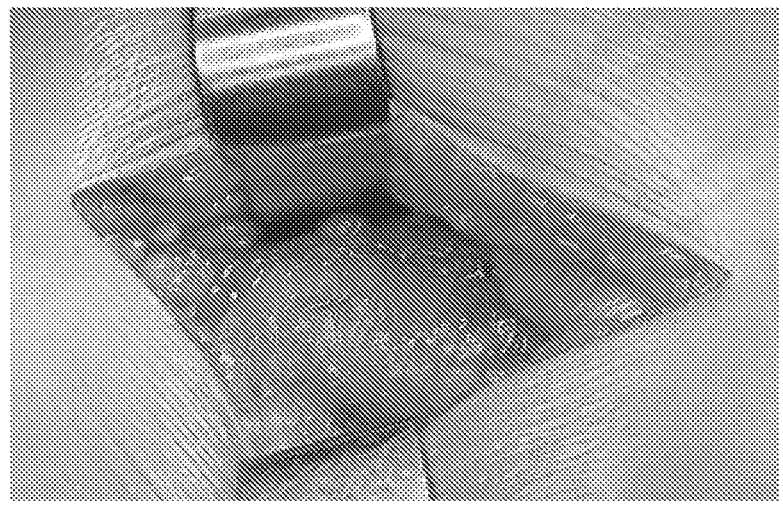
FIG. 6 (Comparative) is a photograph of a retracted incision using a surgical incise drape.

After using conventional surgical prepping procedures, a surgeon placed IOBAN 2 Antimicrobial Incise Drape (a product of 3M Company, St. Paul, Minn.) over the intended surgical site. Following incision, the surgeon used retractors to expose the underlying tissue. Observation of the retracted site showed the skin and draping material to laterally compress causing a large number of wrinkles to form indicative of considerable skin stress as shown in FIG. 6.

Example 2

Figure 7:
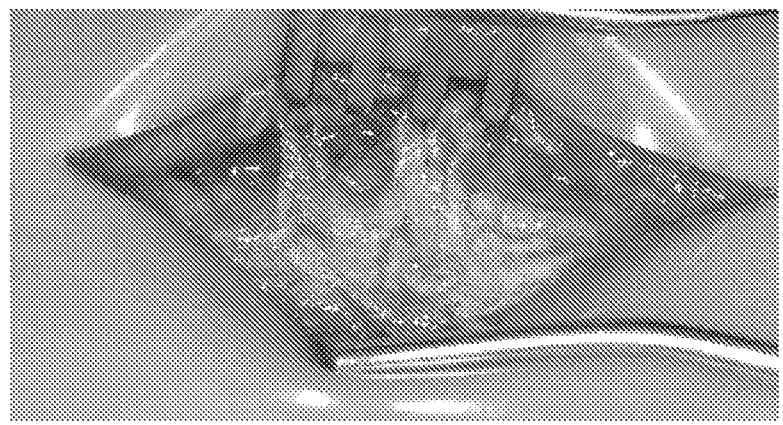
FIG. 7 is a photograph of a retracted incision using a surgical incise drape and a stress-distributing layer of the present invention.

On another patient, the same procedure was followed as in Example 1 with the exception that after placement of the IOBAN 2 Antimicrobial Incise Drape the surgeon centered and attached a TEGADERM Hydrocolloid (a product of 3M Company, St. Paul, Minn.) to the top of the IOBAN drape. After incision and refraction, it was noted that the skin surface surrounding the incisional site did not exhibit stress wrinkles. This indicates that the stress of retraction was being dissipated by the hydrocolloid dressing protecting the skin from compression damage during the course of the surgery. FIG. 7 exemplifies fewer (essentially no) stress wrinkles around the incisional site.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A method of minimizing stress to tissue of a patient during a surgical procedure, the method comprising:
providing a surgical incise drape comprising a flexible polymeric film having opposite first and second major surfaces, and a layer of a pressure sensitive adhesive disposed on at least a portion of the first major surface of the flexible polymeric film;
adhering the surgical incise drape to the patient using the pressure sensitive adhesive layer disposed on the first major surface of the flexible polymeric film;

providing a water-absorbing stress-distributing layer comprising a hydrogel, a hydrocolloid, or a combination thereof; wherein the water-absorbing stress-distributing layer has opposite first and second major surfaces and wherein the water-absorbing stress-distributing layer is at least 2 mm and no more than 8 mm thick between the first and second major surfaces;

attaching the first major surface of the water-absorbing stress-distributing layer to the second major surface of the flexible polymeric film of the surgical incise drape that is adhered to the patient such that the water-absorbing stress-distributing layer conforms to the shape of the tissue of the patient;

making an incision through the water-absorbing stress-distributing layer and the incise drape into the tissue; and retracting the tissue along the incision using a retractor;

wherein the water-absorbing stress-distributing layer reduces stress to the incision and tissue trauma by distributing the forces caused by retraction; and wherein the water-absorbing stress-distributing layer undergoes stretching and/or compression during retraction and protects the skin and underlying tissue from trauma due to compressive and/or stretching forces during tissue retraction.

2. The method of claim 1 wherein attaching the water-absorbing stress-distributing layer comprises attaching the first major surface of the water-absorbing stress-distributing layer to the second major surface of the flexible polymeric film of the surgical incise drape through the use of an intervening pressure sensitive adhesive.

3. The method of claim 1, wherein the retracting does not displace the water-absorbing stress-distributing layer from the patient along the incision while undergoing stretching and/or compression during retraction.

4. The method of claim 1, wherein the surgical procedure is a minimally invasive surgical procedure.

5. The method of claim 1, wherein the surgical procedure is an open surgical procedure.

6. A method of minimizing stress to tissue of a patient during a surgical procedure, the method comprising:

providing a surgical incise drape comprising a flexible polymeric film having opposite first and second major surfaces and a layer of a pressure sensitive adhesive on at least a portion of the first major surface of the flexible polymeric film;

providing a water-absorbing stress-distributing layer comprising a hydrogel, a hydrocolloid, or a combination thereof; wherein the water-absorbing stress-distributing layer has opposite first and second major surfaces and wherein the water-absorbing stress-distributing layer is at least 2 mm and no more than 8 mm thick between the first and second major surfaces;

attaching the first major surface of the water-absorbing stress-distributing layer to the second major surface of the flexible polymeric film of the surgical incise drape so that the surgical incise drape and the water-absorbing stress-distributing layer are attached together to form a stress-distributing composite;

adhering the stress-distributing composite to the patient by contacting the pressure sensitive adhesive layer on the first major surface of the polymeric film of the stress-distributing composite to the patient such that the stress-distributing composite conforms to the shape of the tissue of the patient;

making an incision through the stress-distributing composite into the tissue; and retracting the tissue along the incision using a retractor;

wherein the stress-distributing composite reduces stress to the incision and tissue trauma by distributing the forces caused by retraction; and wherein the stress-distributing composite undergoes stretching and/or compression during retraction and protects the skin and underlying tissue from trauma due to compressive and/or stretching forces during tissue retraction.

7. The method of claim 1, wherein the water-absorbing stress-distributing layer comprises a hydrocolloid.

8. The method of claim 1, wherein the water-absorbing stress-distributing layer is porous.

9. The method of claim 1, wherein the tissue of the patient is initially treated with a presurgical skin preparation.

10. The method of claim 1, wherein the tissue of the patient is initially treated with a barrier film.

11. The method of claim 1 further comprising:

providing a presurgical skin preparation; and treating the patient's skin with a presurgical skin preparation prior to adhering the surgical incise drape to the patient.

12. The method of claim 6 wherein attaching the water-absorbing stress-distributing layer comprises attaching the first major surface of the water-absorbing stress-distributing layer to the second major surface of the flexible polymeric film of the surgical incise drape through the use of an intervening pressure sensitive adhesive so that the surgical incise drape and the water-absorbing stress-distributing layer are attached together to form a stress-distributing composite.

* * * * *